United States Patent
Matsuda et al.

(10) Patent No.: US 8,143,440 B2
(45) Date of Patent: Mar. 27, 2012

(54) METHOD FOR SEPARATION OF OLEFIN-ALCOHOL AZEOTROPIC MIXTURE

(75) Inventors: Yuuki Matsuda, Osaka (JP); Kazuyoshi Ichihara, Osaka (JP); Takeomi Hirasaka, Osaka (JP); Takuya Ichida, Osaka (JP)

(73) Assignee: Daikin Industries, Ltd., Osaka (JP)

( * ) Notice: Subject to any disclaimer, the term of this patent is extended or adjusted under 35 U.S.C. 154(b) by 110 days.

(21) Appl. No.: 12/864,475

(22) PCT Filed: Jan. 9, 2009

(86) PCT No.: PCT/JP2009/050194
§ 371 (c)(1),
(2), (4) Date: Jul. 23, 2010

(87) PCT Pub. No.: WO2009/093487
PCT Pub. Date: Jul. 30, 2009

(65) Prior Publication Data
US 2010/0298595 A1 Nov. 25, 2010

(30) Foreign Application Priority Data
Jan. 25, 2008 (JP) ................ P2008-014861

(51) Int. Cl.
C07C 67/10 (2006.01)
C07C 31/34 (2006.01)
(52) U.S. Cl. .................................. 560/266; 568/842
(58) Field of Classification Search .................. None
See application file for complete search history.

(56) References Cited

U.S. PATENT DOCUMENTS

| 3,239,557 | A | 3/1966 | Fasick et al. |
| 5,118,881 | A | 6/1992 | Vaisbuch et al. |
| 2007/0232766 | A1 | 10/2007 | Hirasaka et al. |
| 2008/0058560 | A1 | 3/2008 | Massell et al. |

FOREIGN PATENT DOCUMENTS

| JP | 39-18112 B1 | 8/1964 |
| JP | 51-149212 A | 12/1976 |
| JP | 59-29047 B2 | 7/1984 |
| JP | 2-240035 A | 9/1990 |
| JP | 2007-520561 A | 7/2007 |
| WO | WO 2005/102984 A1 | 11/2005 |

OTHER PUBLICATIONS

International Search Report dated Mar. 24, 2009 in International Application No. PCT/JP2009/050194.

Primary Examiner — Paul A Zucker
(74) Attorney, Agent, or Firm — Birch, Stewart, Kolasch & Birch, LLP

(57) ABSTRACT

There is provided a method for separating and collecting at least alcohol with a high purity from an azeotropic mixture of olefin and alcohol.

The method conducts the following steps: an azeotropic mixture crystallization step of subjecting an azeotropic mixture of alcohol and olefin represented by the formula: $RfCH=CH_2$ [wherein Rf represents a linear perfluoroalkyl group having 1 to 10 carbon atoms] to a crystallization procedure to separate the mixture into an olefin portion having a higher olefin concentration than that of the original azeotropic mixture and an alcohol portion having a higher alcohol concentration than that of the original azeotropic mixture; and an alcohol purification step of subjecting the separated alcohol portion to either a crystallization procedure or a distillation procedure to separate the alcohol portion into a low-alcohol portion having a lower alcohol concentration than that of the original alcohol portion and a high-alcohol portion having a higher alcohol concentration than that of the original alcohol portion, and thereby collecting alcohol as the high-alcohol portion.

7 Claims, 1 Drawing Sheet

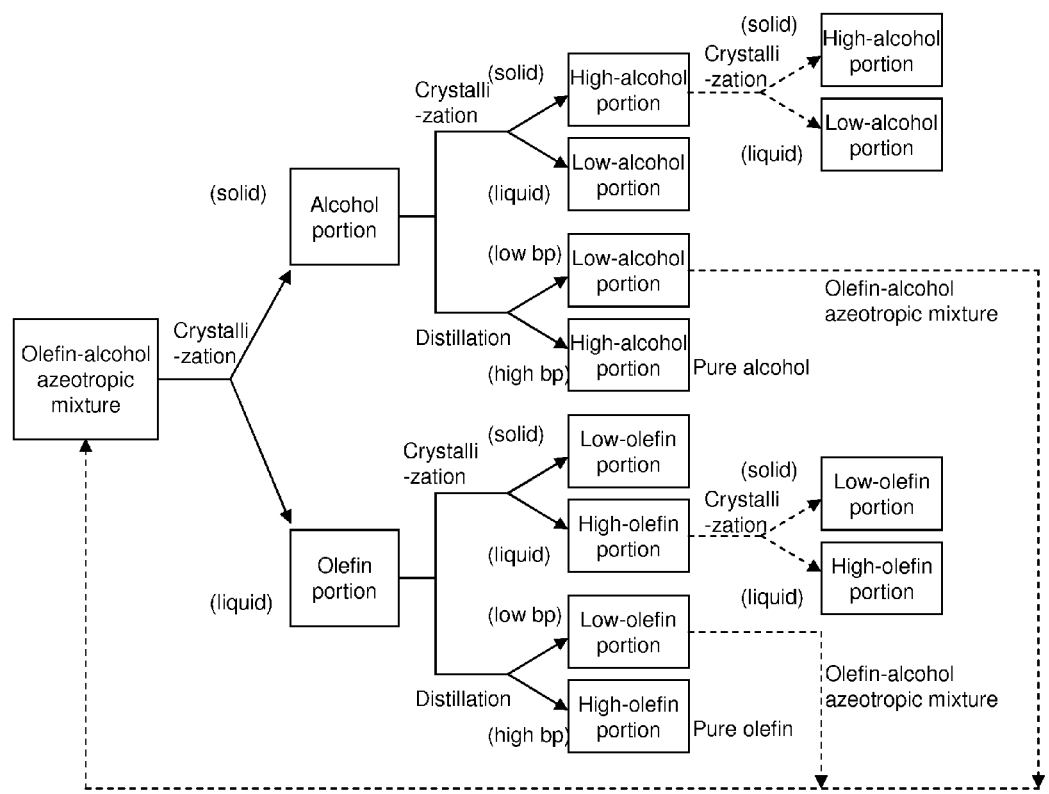

METHOD FOR SEPARATION OF OLEFIN-ALCOHOL AZEOTROPIC MIXTURE

TECHNICAL FIELD

The present invention relates to a method for separation of an olefin-alcohol azeotropic mixture, more specifically to a method for separating and collecting at least alcohol from an azeotropic mixture of olefin and alcohol. The present invention also relates to a process for producing ester which utilizes such method.

BACKGROUND ART

Esters having a structure represented by a formula $RfCH_2CH_2OCOR$ are used as, for example, intermediates for producing water- and oil-repellent agents, surfactants, mold release agents, and other useful substances.

As a process for synthesizing such esters, a known process is to heat a halogenated compound represented by a formula $RfCH_2CH_2Y$ (Y is Br or I) and an alkali metal salt of carboxylic acid in an alcohol solvent (See Patent Citation 1). After the esterification reaction, a reaction mixture comprising by-products, alcohol as the solvent and so on in addition to ester as the target product can be subjected to a rectification procedure to obtain the target ester.

Suitable alcohols used in the above ester synthesizing process (for example, tert-amyl alcohol, tert-butyl alcohol, and the like) are relatively expensive, thus it is preferred that alcohol is collected as much as possible after the reaction and reused as the solvent for the esterification reaction.

Patent Citation 1: JP 39-18112 B1
Patent Citation 2: JP 59-29047 B2

DISCLOSURE OF INVENTION

Technical Problem

A major by-product in the above esterification reaction is olefin represented by a formula $RfCH=CH_2$, which may generate as a by-product at a ratio of about 10-20% by mole (based on the reaction mixture obtained after the reaction). Since such olefin ($RfCH=CH_2$) and alcohol of the solvent cause azeotropic boiling, it is not possible to separate them completely from each other by a rectification procedure.

When alcohol mixed with such olefin ($RfCH=CH_2$) is used as the solvent for the esterification reaction, this causes a lower yield of the target product. Therefore, an azeotropic mixture of olefin and alcohol obtained by the rectification procedure of the reaction mixture can not be reused as the solvent for the esterification reaction. This brings about a poor alcohol consumption rate and a considerable amount of a fluorine-containing waste fluid in the ester ($RfCH_2CH_2OCOR$) production, which has become a big problem in the ester production process. If alcohol can be separated with a high purity from the azeotropic mixture of olefin and alcohol, it will be beneficial to reuse the separated alcohol for the esterification reaction.

The primary purpose of the present invention is to provide a method which can separate and collect at least alcohol with a high purity from an azeotropic mixture of olefin and alcohol.

Technical Solution

The inventors has focused on the difference in a melting point between alcohol and olefin ($RfCH=CH_2$), and considered a process for separating them from each other by utilizing a so-called crystallization. According to a usual separation by crystallization, one step of the crystallization procedure can separate a high-melting point component in the form of solid with a high purity from an azeotropic mixture (See, for example, Patent Citation 2). That is, in a case of a general azeotropic mixture (two-component system), a solid precipitated by one step of the crystallization procedure is a pure solid of one of the components.

However, the research by the inventors has found that in a case of a mixture of alcohol and olefin ($RfCH=CH_2$), only one step of the crystallization procedure can not separate a high-melting point component, which is generally alcohol, in the form of solid with a high purity, and the precipitated solid is a mixed solid of these two components. A composition of the precipitated solid varies depending on a composition of a mother liquid. The higher the alcohol concentration of the original mixture, the higher the alcohol concentration of the precipitated solid. Based on such unique findings, the inventors have completed the present invention.

In one aspect of the present invention, there is provided a method for separating and collecting at least alcohol from an azeotropic mixture of olefin and alcohol, which comprises:

an azeotropic mixture crystallization step of subjecting an azeotropic mixture of alcohol and olefin represented by a following formula:

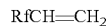

wherein Rf is a linear perfluoroalkyl group having 1 to 10 carbon atoms, to a crystallization procedure to separate the azeotropic mixture into an olefin portion having a higher olefin concentration than that of the original azeotropic mixture and an alcohol portion having a higher alcohol concentration than that of the original azeotropic mixture; and an alcohol purification step of subjecting the separated alcohol portion to either a crystallization procedure or a distillation procedure to separate the alcohol portion into a low-alcohol portion having a lower alcohol concentration than that of the original alcohol portion and a high-alcohol portion having a higher alcohol concentration than that of the original alcohol portion, and thereby collecting alcohol as the high-alcohol portion.

In this method of the present invention (hereinafter also referred to as the method for separation of an olefin-alcohol azeotropic mixture), the alcohol portion having a higher alcohol concentration than that of the original azeotropic mixture is firstly obtained in the azeotropic mixture crystallization step, and then the high-alcohol portion having a further higher alcohol concentration than that of the alcohol portion is obtained by a crystallization procedure or a distillation procedure in the following alcohol purification step. Therefore, according to the method of the present invention, it is possible to collect alcohol with a high purity.

Throughout the present invention, the "crystallization procedure" means a separation procedure utilizing a difference between a composition of a liquid phase and a composition of a solid phase, wherein a mixture as an object of the procedure (for example in the present invention, an azeotropic mixture for the azeotropic mixture crystallization step, and an alcohol portion for the alcohol purification step) initially in a liquid state is gradually cooled to precipitate a solid, and the precipitated solid is removed from the mother liquid so that this solid portion (or the portion derived from the solid) and a residue left after the removal of the solid are separated from each other. In comparison to the original mixture, the portion derived from the solid has a higher concentration of a high-melting point component, whereas the portion derived from the residue left after the removal of the solid has a higher concentration of a low-melting point component. In a case of a two-component olefin-alcohol system, generally the high-melting point component is alcohol, and the low-melting point component is olefin (RfCH=CH$_2$), although the present invention is not limited thereto.

The "distillation procedure" means a separation procedure utilizing a difference between a composition of a liquid phase and a composition of vapor phase. Any process generally known as such in the art can be applied.

In the present invention, after the alcohol portion separated in the azeotropic mixture crystallization step is subjected to either a crystallization procedure or a distillation procedure in the alcohol purification step, each of portions obtained thereby may be further subjected to a crystallization, a distillation procedure and so on, if necessary.

For example, when the crystallization procedure is conducted in the alcohol purification step, the crystallization procedure may be repeated to reach the desired purity of alcohol.

When the distillation procedure is conducted in the alcohol purification step, the low-alcohol portion is an azeotropic mixture of olefin and alcohol, and the high-alcohol portion consists essentially of alcohol. Since the composition of the alcohol portion to be subjected to the distillation procedure has a higher alcohol concentration than that of the azeotropic mixture by the former azeotropic mixture crystallization step, the distillation procedure can give the high-alcohol portion consisting essentially of alcohol (hereinafter also referred to as pure alcohol). In this case, the high-alcohol portion (pure alcohol) may have an alcohol concentration of, for example, 100% by mole analytically (existence of olefin is below a detection limit by gas chromatographic analysis).

In addition, the azeotropic mixture of olefin and alcohol obtained by this distillation procedure may be returned to the azeotropic mixture crystallization step. It becomes possible by such circulation to avoid wasting the azeotropic mixture of olefin and alcohol and collect alcohol as much as possible.

In one embodiment of the present invention, the method of the present invention further comprises an olefin purification step of subjecting the olefin portion separated in the azeotropic mixture crystallization step to either a crystallization procedure or a distillation procedure to separate the olefin portion into a low-olefin portion having a lower olefin concentration than that of the original olefin portion and a high-olefin portion having a higher olefin concentration than that of the original olefin portion, and thereby collecting olefin as the high-olefin portion.

According to this embodiment, the olefin portion having a higher olefin concentration than that of the original azeotropic mixture is firstly obtained in the azeotropic mixture crystallization step, and then the high-olefin portion having a further higher olefin concentration than that of the olefin portion is obtained by a crystallization procedure or a distillation procedure in the following olefin purification step. Therefore, according to this embodiment of the present invention, it is also possible to collect olefin (RfCH=CH$_2$) with a high purity.

In the above embodiment, after the olefin portion separated in the azeotropic mixture crystallization step is subjected to either a crystallization procedure or a distillation procedure in the olefin purification step, each of portions obtained thereby may be further subjected to a crystallization, a distillation procedure and so on, if necessary.

For example, when the crystallization procedure is conducted in the olefin purification step, the crystallization procedure may be repeated to reach the desired purity of olefin.

When the distillation procedure is conducted in the olefin purification step, the low-olefin portion is an azeotropic mixture of olefin and alcohol, and the high-olefin portion consists essentially of olefin. Since the composition of the olefin portion to be subjected to the distillation procedure has a higher olefin concentration than that of the azeotropic mixture by the former azeotropic mixture crystallization step, the distillation procedure can give the high-olefin portion consisting essentially of olefin (hereinafter also referred to as pure olefin). In this case, the high-olefin portion (pure olefin) may have an olefin concentration of, for example, 100% by mole analytically (existence of alcohol is below a detection limit by gas chromatographic analysis).

In addition, the azeotropic mixture of olefin and alcohol obtained by this distillation procedure may be returned to the azeotropic mixture crystallization step. It becomes possible by such circulation to avoid wasting the azeotropic mixture of olefin and alcohol and collect alcohol and olefin as much as possible.

In the alcohol purification step and the olefin purification step, the crystallization procedure may be conducted as described in the above, but it is more preferable to conduct the distillation procedure since pure alcohol and pure olefin can be conveniently obtained in the respective steps. Also, the crystallization procedure and the distillation procedure may be combined together in the alcohol purification step, for example, it is preferable to conduct the crystallization procedure at least once followed by the distillation procedure.

The method for separation of an olefin-alcohol azeotropic mixture of the present invention can be preferably utilized for an ester production process. In another aspect of the present invention, there is also provided a process for producing ester by reacting in an alcohol solvent a halogenated compound represented by a following formula:

wherein Rf is a linear perfluoroalkyl group having 1 to 10 carbon atoms, and Y is bromine or iodine, and an alkali metal salt of carboxylic acid represented by a following formula:

wherein RCOO is a residue excluding a nucleophilic substituent from one of mono- or poly-carboxylic organic acids, and X is an alkali metal, to generate ester represented by a following formula:

characterized in that a reaction mixture comprising the ester generated by the reaction, olefin generated as a by-product during the reaction, and alcohol used as the solvent is subjected to a distillation procedure to obtain an azeotropic mixture of olefin and alcohol, and the obtained azeotropic mixture of olefin and alcohol is subjected to the above described method for separation of the olefin-alcohol azeotropic mixture of the present invention to collect alcohol, the collected alcohol is reused as the solvent for the reaction.

According to this ester production process of the present invention, alcohol as the solvent can be reused without lowering a yield of ester (RfCH$_2$CH$_2$OCOR) as the target product, so that an alcohol consumption rate and therefore an efficiency in the production can be improved. When the distillation procedure is used for the purification in the present invention, the azeotropic mixture of olefin and alcohol can be generated, it can be returned to the azeotropic mixture crystallization step, and therefore there is no need to waste it. Additionally, when olefin ($RfCH=CH_2$) is also collected with a high purity as well as alcohol, such olefin has an added value, and therefore there is also no need to waste it.

ADVANTAGEOUS EFFECTS

According to the present invention, there is provided the method for separating and collecting at least alcohol with a high purity from an azeotropic mixture of olefin and alcohol. When this method for separation of an olefin-alcohol azeotropic mixture of the present invention is utilized for an ester production process, alcohol as the solvent can be reused without lowering a yield of ester as the target product, so that an efficiency in the production can be improved, and preferably an amount of a fluorine-containing waste fluid can be reduced.

BRIEF DESCRIPTION OF DRAWINGS

FIG. 1 shows a chart for explaining the method for separation of an olefin-alcohol azeotropic mixture in one embodiment of the present invention (bp: boiling point).

BEST MODE FOR CARRYING OUT THE INVENTION

Embodiment 1

The method for separation of an olefin-alcohol azeotropic mixture in one embodiment of the present invention is hereinafter described with reference to FIG. 1.

As the olefin-alcohol azeotropic mixture, the used azeotropic mixture consists of two components of olefin and alcohol and has an azeotropic composition. This olefin is represented by a following formula.

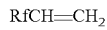

$RfCH=CH_2$

In the formula, Rf is a linear perfluoroalkyl group having 1 to 10 carbon atoms, more specifically Rf is represented by $F(CF_2)_n-$ wherein n is an integer of 1 to 10, preferably an integer of 4 to 8, for example 6. On the other hand, alcohol may be any alcohol as long as it causes azeotropic boiling with such olefin.

In this embodiment, the used olefin-alcohol azeotropic mixture causes azeotropic boiling at the minimum boiling point (minimum boiling azeotropic mixture), wherein a melting point of alcohol is higher than that of olefin, and of which alcohol concentration at a solidified state is higher than that at a liquid state. As an example of such olefin-alcohol azeotropic mixture, there is an azeotropic mixture of perfluorohexylethylene ($F(CF_2)_6CH=CH_2$) and tert-butyl alcohol (hereinafter also simply referred to as t-butanol in this specification).

Azeotropic Mixture Crystallization Step

Referring to FIG. 1, the olefin-alcohol azeotropic mixture is subjected to a crystallization procedure to be separated into an olefin portion having a relatively higher olefin concentration and an alcohol portion having a relatively higher alcohol concentration. AS to the two-component olefin ($RfCH=CH_2$)-alcohol system, a composition of a solid phase obtained from the liquid phase having an azeotropic composition differs from the azeotropic composition, and therefore the crystallization procedure can separate the azeotropic mixture into the olefin portion having a higher olefin concentration and the alcohol portion having a higher alcohol concentration in comparison to the original azeotropic mixture.

In this embodiment, more specifically, the azeotropic mixture is firstly cooled to a temperature less than the melting point of alcohol, which is a high-melting point component. The solid precipitated thereby has a higher alcohol concentration than that of the original azeotropic mixture, and the liquid residue has a higher olefin concentration than that of the original azeotropic mixture. Any suitable solid-liquid separation is conducted to separate the resultant into the solid portion and the liquid residue so that this solid portion is obtained as an alcohol portion and the liquid residue is obtained as an olefin portion (it is noted that the alcohol portion is returned into a liquid state from the solid slate).

As to the two-component olefin($RfCH=CH_2$)-alcohol system, the precipitated solid does not consist of pure alcohol but a mixture of alcohol and olefin. For example, in a case of an azeotropic mixture of perfluorohexylethylene and t-butanol (about 65% by weight of perfluorohexylethylene and about 35% by weight of t-butanol), a solid (thus an alcohol portion) obtained from this azeotropic mixture may have a composition of about 30% by weight of perfluorohexylethylene and about 70% by weight of t-butanol.

Alcohol Purification Step

The alcohol portion obtained by the azeotropic mixture crystallization step is subjected to a crystallization procedure or a distillation procedure as described below, to be separated into a high-alcohol portion having a relatively high alcohol concentration and a low-alcohol portion having a relatively low alcohol concentration.

(1) Crystallization Procedure

It is possible by subjecting the alcohol portion to a further crystallization procedure to separate the alcohol portion into the high-alcohol portion and the low-alcohol portion. As to the two-component olefin($RfCH=CH_2$)— alcohol system, depending on the crystallization conditions, but generally the alcohol concentration of the precipitated solid tends to increase as the alcohol concentration of the original mixture increases. Thus, the high-alcohol portion having a higher alcohol concentration than that of the original mixture can be obtained.

Specific procedure may be conducted similarly to the crystallization procedure in the former azeotropic mixture crystallization step. The solid portion is obtained as the high-alcohol portion and the liquid residue is obtained as the low-alcohol portion (it is noted that the high-alcohol portion is returned into a liquid state from the solid slate).

If the alcohol concentration of the obtained high-alcohol portion is not sufficiently high, the crystallization procedure may be repeated until the desired purity of alcohol is attained, but preferably the high alcohol portion is subjected to a distillation procedure similar to that described in the following section (2). On the other hand, the low-alcohol portion is, although this embodiment is not limited thereto, preferably subjected to a distillation procedure similar to that described in the following section (4).

(2) Distillation Procedure

Alternatively, it is also possible by subjecting the alcohol portion to a distillation procedure to separate the alcohol portion into the high-alcohol portion and the low-alcohol portion. The alcohol portion obtained through the former azeotropic mixture crystallization step has a composition different from the azeotropic composition, and therefore it is possible by subjecting the alcohol portion to a distillation procedure to obtain the high-alcohol portion having a higher alcohol concentration than that of the original mixture.

In this embodiment, more specifically, an olefin-alcohol minimum boiling azeotropic mixture is obtained as a low-boiling point component, and pure alcohol is obtained as a high-boiling point component. The former corresponds to the low-alcohol portion, and the latter corresponds to the high-alcohol portion. Thus obtained olefin-alcohol minimum boiling azeotropic mixture can be returned to the azeotropic mixture crystallization procedure to increase a collection rate of alcohol, and besides to eliminate a procedure and cost required for the waste of it.

After the above (1) Crystallization procedure or (2) Distillation procedure, it is possible to separate and collect alcohol with a high purity in the form of the high-alcohol portion.

Olefin Purification Step

The olefin portion obtained by the azeotropic mixture crystallization step is subjected to a crystallization procedure or a distillation procedure as described below, to be separated into a high-olefin portion having a relatively high olefin concentration and a low-olefin portion having a relatively low olefin concentration.

(3) Crystallization Procedure

It is possible by subjecting the olefin portion to a further crystallization procedure to separate the olefin portion into the high-olefin portion and the low-olefin portion. As to the two-component olefin(RfCH=CH$_2$)— alcohol system, depending on the crystallization conditions, but generally the olefin concentration of the left liquid residue tends to increase as the olefin concentration of the original mixture increases. Thus, the high-olefin portion having a higher olefin concentration than that of the original mixture can be obtained.

Specific procedure may be conducted similarly to the crystallization procedure in the former azeotropic mixture crystallization step. The solid portion is obtained as the low-olefin portion and the liquid residue is obtained as the high-olefin portion.

If the olefin concentration of the obtained high-olefin portion is not sufficiently high, the crystallization procedure may be repeated until the desired purity of olefin is attained, but preferably the high olefin portion is subjected to a distillation procedure similar to that described in the following section (4). On the other hand, the low-olefin portion is, although this embodiment is not limited thereto, preferably subjected to a distillation procedure similar to that described in the above section (2).

(4) Distillation Procedure

Alternatively, it is also possible by subjecting the olefin portion to a distillation procedure to separate the olefin portion into the high-olefin portion and the low-olefin portion. The olefin portion obtained through the former azeotropic mixture crystallization step has a composition different from the azeotropic composition, and therefore it is possible by subjecting the olefin portion to a distillation procedure to obtain the high-olefin portion having a higher olefin concentration than that of the original mixture.

In this embodiment, more specifically, an olefin-alcohol minimum boiling azeotropic mixture is obtained as a low-boiling point component, and pure olefin is obtained as a high-boiling point component. The former corresponds to the low-olefin portion, and the latter corresponds to the high-olefin portion. Thus obtained olefin-alcohol minimum boiling azeotropic mixture can be returned to the azeotropic mixture crystallization procedure to increase a collection rate of alcohol, and besides to eliminate a procedure and cost required for the waste of it.

After the above (3) Crystallization procedure or (4) Distillation procedure, it is possible to separate and collect olefin with a high purity in the form of the high-olefin portion.

According to this embodiment, it is possible to separate and collect both alcohol and olefin with high purities from the azeotropic mixture of olefin and alcohol.

This embodiment is described about the olefin-alcohol azeotropic mixture which causes azeotropic boiling at the minimum boiling point (minimum boiling azeotropic mixture), wherein the melting point of alcohol is higher than that of olefin, and of which alcohol concentration at a solidified state is higher than that at a liquid state. It should be noted that, however, the present invention is not limited to such embodiment, and any suitable olefin-alcohol azeotropic mixture may be used. As to each of alcohol and olefin, the fact that, for example, it is distributed more into a solid phase or a liquid phase by a crystallization procedure, and distributed more into a liquid phase or a vapor phase by a distillation procedure may differ depending on the system of an olefin-alcohol azeotropic mixture used. (The reason why the words of solid, liquid, low bp, high by in FIG. 1 are shown in parentheses is to intend that the present invention is not limited to this embodiment.)

Embodiment 2

The process for producing ester in one embodiment of the present invention is hereinafter described.

Reaction Step

At first, a halogenated compound and an alkali metal salt of carboxylic acid are reacted with each other in an alcohol solvent to generate ester.

The halogenated compound as a raw material is represented by a following formula.

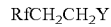
RfCH$_2$CH$_2$Y

In the formula, Y is bromine or iodine. Also in the formula, Rf is a linear perfluoroalkyl group having 1 to 10 carbon atoms, more specifically Rf is represented by F(CF$_2$)$_n$— wherein n is an integer of 1 to 10, preferably an integer of 4 to 8, for example 6.

The alkali metal salt of carboxylic acid as the other raw material is represented by a following formula.

RCOOX

In the formula, RCOO is a residue excluding a nucleophilic substituent from one of mono- or poly-carboxylic organic acids, for example, a residue from acids such as formic acid, acetic acid, propionic acid, butyric acid, pivalic acid, valeric acid, caproic acid, pelargonic acid, caprylic acid, capric acid, lauric acid, myristic acid, palmitic acid, stearic acid, enanthic acid, hexahydrobenzoic acid, camphor acid, acrylic acid, methacrylic acid, a-chloroacrylate, crotonic acid, tiglic acid, vinyl acetic acid, oleic acid, undecylenic acid, brassidic acid, succinic acid, glutaric acid, adipic acid, pimelic acid, suberic acid, azelaic acid, sebacic acid, maleic acid, fumaric acid, citraconic acid, benzoic acid, nitrobenzoic acid, naphthoic acid, phenylacetic acid, naphthylacetic acid, phthalic acid, isophthalic acid, terephthalic acid, chlorobenzoic acid, toluic acid, cinnamic acid, trimellitic acid, trimesinic acid, pyromellitic acid, naphthalic acid (1,4 and 1,8), and so on. Also in the formula, X is an alkali metal, for example, lithium, sodium, or potassium.

Among them, preferred are alkali metal salts of acrylic acid and methacrylic acid, and more preferred are potassium salts of them.

Alcohol as the solvent is not limited as long as it causes azeotropic boiling with such olefin. For example, a monovalent alcohol having a dielectric constant not larger than about 17.5 at 25° C. as described in Patent Citation 1, more specifically, n-amyl alcohol, n-hexyl alcohol, n-octyl alcohol, sec-butyl alcohol, n-butyl alcohol, isobutyl alcohol, tert-butyl alcohol, isoamyl alcohol, tert-amyl alcohol, n-heptyl alcohol, benzyl alcohol, α-phenylethyl alcohol, β-phenylethyl alcohol, n-nonyl alcohol, n-decyl alcohol, n-dodecyl alcohol, n-tetradecyl alcohol, cetyl alcohol and octadecyl alcohol, and 2-heptanol, 3-heptanol, 4-heptanol, 2-pentanol, 3-pentanol, 3-methylpentanol, cyclohexanol, triethyl carbinol, 2-, 3- and 4-methyl-1-cyclohexanol, 2-, 3- and 4-octanol, 2-, 3-, 4-, 5- and 6-methyl-1-heptanol, 2-, 3- and 4-methyl-4-heptanol, 1,2,3,4-tetrahydro-2-naphthol, 2-ethyl-1-hexanol, and so on.

Among them, preferred are tert-amyl alcohol and tert-butyl alcohol, and more preferred is tert-butyl alcohol (i.e. t-butanol) in view of its availability and price.

This reaction generates ester which is represented by a following formula.

RfCH$_2$CH$_2$OCOR

During this esterification reaction, also generated as a by-product is olefin which is represented by a following formula.

RfCH=CH$_2$

In these formulae, Rf and R are those described in the above.

For this reaction step, conditions such as a temperature, a pressure and a time period can be set appropriately.

Thus, a reaction mixture comprising the ester generated by the reaction, the olefin generated as a by-product during the reaction, and the alcohol used as the solvent is obtained.

Distillation Step

The reaction mixture obtained by the former reaction step is subjected to a distillation (rectification) procedure. Thus, a fraction essentially consisting of the target ester is obtained, and also a fraction consisting of an olefin-alcohol azeotropic mixture is generated.

For example, in a case of olefin being perfluorohexylethylene and alcohol being t-butanol, there is generated a minimum boiling azeotropic mixture having a composition of about 65% by weight of perfluorohexylethylene and about 35% by weight of t-butanol.

For this distillation step, conditions such as a temperature and a pressure can be set appropriately.

Alcohol Separation and Collection Step

From the olefin-alcohol azeotropic mixture obtained by the former distillation step, alcohol is separated and corrected by the method for separation of an olefin-alcohol azeotropic mixture as, for example, described in the Embodiment 1. The collected alcohol can be reused as the solvent for the esterification reaction in the reaction step.

Also in this step, olefin can be separated and collected, and the collected olefin has a value itself and may be used as, for example, a modifier (or denaturant) for a resin. Otherwise, olefin added with H$_2$ can be used as a heat medium, or olefin added with HI or HBr can be reused as the raw material of the esterification reaction.

According to this embodiment, alcohol having a high purity can be reused as the solvent, so that an efficiency in the ester production can be improved without lowering a yield of ester as the target product. Further, the olefin-alcohol azeotropic mixture, which had to be wasted in the conventional ester production process, can be reused, so that an amount of a fluorine-containing waste fluid can be effectively reduced and preferably the waste fluid can be eliminated.

However, the method for separation of an olefin-alcohol azeotropic mixture of the present invention is applicable not only to the ester production process but also to any other cases.

Examples

In order to confirm that the present invention exerts the effects, olefin-alcohol mixtures having different compositions were subjected to the crystallization procedure.

As mixtures of perfluorohexylethylene (F(CF$_2$)$_6$CH=CH$_2$) and t-butanol, four mixture samples having different compositions shown in the column of Sample of Table 1 were prepared.

It is noted that perfluorohexylethylene is liquid at ordinary temperature (15° C.) and has a melting point less that −20° C. (a specific melting point is unknown), whereas t-butanol is solid at ordinary temperature (15° C.) and has a boiling point of about 83° C. and a melting point of about 25° C. Between perfluorohexylethylene and t-butanol, a high-boiling point component is t-butanol.

A constant-temperature container was previously purged with nitrogen, and 300 to 400 mL of the mixture sample was put therein and gradually cooled at a rate of 5 to 6° C./hr with being stirred. A temperature at which precipitation of solid was firstly observed was determined as a precipitation temperature. Then, after the temperature was once raised to melt the whole of the mixture, the mixture was gradually cooled again so that the precipitation was reconfirmed. The cooling was continued to increase an amount of solid, and then kept at a temperature (corresponding to a temperature for the following sample taking) slightly lower than the precipitation temperature for at least 30 minutes. After that, a sample taken from the mixture was subjected to solid-liquid separation by a glass filter. The respective compositions of thus obtained liquid and solid were analyzed by gas chromatography.

The above procedures were conducted for each of the mixture samples as Tests 1 to 4. The results are shown in Tables 1 and 2.

TABLE 1

| | t-butanol/perfluorohexylethylene (wt %/wt %) | | |
|---|---|---|---|
| | Sample | Liquid | Solid |
| Test 1 | 43.2/56.8 | 29.1/70.9 | 83.9/16.1 |
| Test 2 | 36.9/63.1 | 29.1/70.9 | 70.7/29.3 |
| Test 3 | 23.7/76.3 | 15.2/84.8 | 57.9/42.1 |
| Test 4 | 0.0/100.0 | —/— | —/— |

TABLE 2

| | Temperature (° C.) | |
|---|---|---|
| | Precipitation | Sample Taking |
| Test 1 | 16.5 | 14.8 |
| Test 2 | 15 | 13.8 |
| Test 3 | 12.5 | 9.9 |
| Test 4 | — | — |

From Tests 1 to 3, it was confirmed that the precipitated solid did not consist of only one component of alcohol as the high-boiling point component but was mixed with a considerable amount of olefin, and that the higher the alcohol concentration of the original mixture, the higher the alcohol concentration of the precipitated solid.

INDUSTRIAL APPLICABILITY

The method for separation of an olefin-alcohol azeotropic mixture of the present invention is applicable to produce esters used as, for example, intermediates for producing water- and oil-repellent agents, surfactants, mold release agents, and other useful substances.

The invention claimed is:

1. A method for separating and collecting at least alcohol from an azeotropic mixture of olefin and alcohol, which comprises:

an azeotropic mixture crystallization step of subjecting an azeotropic mixture of alcohol and olefin represented by a following formula:

$$RfCH=CH_2$$

wherein Rf is a linear perfluoroalkyl group having 1 to 10 carbon atoms, to a crystallization procedure to separate the azeotropic mixture into an olefin portion having a higher olefin concentration than that of the original azeotropic mixture and an alcohol portion having a higher alcohol concentration than that of the original azeotropic mixture; and an alcohol purification step of subjecting the separated alcohol portion to either a crystallization procedure or a distillation procedure to separate the alcohol portion into a low-alcohol portion having a lower alcohol concentration than that of the original alcohol portion and a high-alcohol portion having a higher alcohol concentration than that of the original alcohol portion, and thereby collecting alcohol as the high-alcohol portion.

2. The method according to claim 1, wherein the distillation procedure is conducted in the alcohol purification step, the low-alcohol portion is an azeotropic mixture of olefin and alcohol, and the high-alcohol portion consists essentially of alcohol.

3. The method according to claim 2, wherein the azeotropic mixture of olefin and alcohol obtained by the distillation procedure in the alcohol purification step is returned to the azeotropic mixture crystallization step.

4. The method according to claim 1, which further comprises an olefin purification step of subjecting the olefin portion separated in the azeotropic mixture crystallization step to either a crystallization procedure or a distillation procedure to separate the olefin portion into a low-olefin portion having a lower olefin concentration than that of the original olefin portion and a high-olefin portion having a higher olefin concentration than that of the original olefin portion, and thereby collecting olefin as the high-olefin portion.

5. The method according to claim 4, wherein the distillation procedure is conducted in the olefin purification step, the low-olefin portion is an azeotropic mixture of olefin and alcohol, and the high-olefin portion consists essentially of olefin.

6. The method according to claim 5, wherein the azeotropic mixture of olefin and alcohol obtained by the distillation procedure in the olefin purification step is returned to the azeotropic mixture crystallization step.

7. A process for producing ester by reacting in an alcohol solvent a halogenated compound represented by a following formula:

$$RfCH_2CH_2Y$$

wherein Rf is a linear perfluoroalkyl group having 1 to 10 carbon atoms, and Y is bromine or iodine, and an alkali metal salt of carboxylic acid represented by a following formula:

$$RCOOX$$

wherein RCOO is a residue excluding a nucleophilic substituent from one of mono- or poly-carboxylic organic acids, and X is an alkali metal, to generate ester represented by a following formula:

$$RfCH_2CH_2OCOR$$

characterized in that a reaction mixture comprising the ester generated by the reaction, olefin generated as a by-product during the reaction, and alcohol used as the solvent is subjected to a distillation procedure to obtain an azeotropic mixture of olefin and alcohol, and the obtained azeotropic mixture of olefin and alcohol is subjected to the method according to claim 1 to collect alcohol, the collected alcohol is reused as the solvent for the reaction.

* * * * *